United States Patent
Early et al.

(10) Patent No.: US 11,607,314 B2
(45) Date of Patent: Mar. 21, 2023

(54) METHOD AND APPARATUS FOR BONE FIXATION

(71) Applicant: Biomet C.V., Warsaw, IN (US)

(72) Inventors: John Early, Dallas, TX (US); Brian Berelsman, Warsaw, IN (US); Adam Finley, Winona Lake, IN (US); Paul D'Antonio, Winona Lake, IN (US)

(73) Assignee: Biomet C.V., Warsaw, IN (US)

(*) Notice: Subject to any disclaimer, the term of this patent is extended or adjusted under 35 U.S.C. 154(b) by 430 days.

(21) Appl. No.: 16/456,379

(22) Filed: Jun. 28, 2019

(65) Prior Publication Data
US 2019/0321183 A1    Oct. 24, 2019

Related U.S. Application Data

(62) Division of application No. 14/520,441, filed on Oct. 22, 2014, now Pat. No. 10,383,733.

(51) Int. Cl.
*A61F 2/30* (2006.01)
*A61B 17/80* (2006.01)
(Continued)

(52) U.S. Cl.
CPC ............ *A61F 2/30* (2013.01); *A61B 17/0642* (2013.01); *A61B 17/7044* (2013.01);
(Continued)

(58) Field of Classification Search
CPC ... A61F 2002/30622; A61F 2002/4212; A61B 17/8095
See application file for complete search history.

(56) References Cited

U.S. PATENT DOCUMENTS

| 5,395,372 A | * | 3/1995 | Holt ................... A61B 17/7059 606/75 |
| 7,887,595 B1 | | 2/2011 | Pimenta |

(Continued)

FOREIGN PATENT DOCUMENTS

| CN | 102137638 A | 7/2011 |
| CN | 104010595 A | 8/2014 |

(Continued)

OTHER PUBLICATIONS

"U.S. Appl. No. 14/520,441 Response filed Feb. 9, 2017 to Non Final Office Action dated Sep. 9, 2016", 13 pgs.
(Continued)

*Primary Examiner* — Megan Y Wolf
(74) *Attorney, Agent, or Firm* — Schwegman Lundberg & Woessner, P.A.

(57) ABSTRACT

An orthopedic implant can be used for fixation of a joint or fracture and can include a tapered member and at least one fixation member. The tapered member can be configured for placement in association with one or more bone segments. The tapered member can have a longitudinally extending body that defines an upper surface portion, an opposed lower surface portion and first and second sides, where at least the first and second sides can be formed of porous metal and can have a porous metal outer surface. The at least one fixation member can be integrally formed with the tapered member and can extend laterally outwardly from the tapered member body. The at least one fixation member can be configured to secure the implant to the one or more bone segments to provide fixation of the one or more bone segments relative to the tapered member.

8 Claims, 9 Drawing Sheets

(51) Int. Cl.
  *A61B 17/064* (2006.01)
  *A61B 17/70* (2006.01)
  *A61F 2/42* (2006.01)

(52) U.S. Cl.
  CPC ...... *A61B 17/7059* (2013.01); *A61B 17/8061* (2013.01); *A61B 17/8095* (2013.01); *A61F 2002/30011* (2013.01); *A61F 2002/3092* (2013.01); *A61F 2002/30266* (2013.01); *A61F 2002/30622* (2013.01); *A61F 2002/4212* (2013.01); *A61F 2310/00011* (2013.01)

(56) References Cited

U.S. PATENT DOCUMENTS

| | | | |
|---|---|---|---|
| 10,383,733 | B2 | 8/2019 | Early et al. |
| 2002/0077702 | A1 | 6/2002 | Castro |
| 2003/0032961 | A1* | 2/2003 | Pelo ........................ A61L 27/18 606/232 |
| 2005/0075641 | A1 | 4/2005 | Singhatat et al. |
| 2005/0177238 | A1 | 8/2005 | Khandkar et al. |
| 2005/0177245 | A1 | 8/2005 | Leatherbury et al. |
| 2006/0036251 | A1 | 2/2006 | Reiley |
| 2006/0036322 | A1 | 2/2006 | Reiley |
| 2006/0058802 | A1 | 3/2006 | Kofoed |
| 2007/0156241 | A1 | 7/2007 | Reiley et al. |
| 2007/0198016 | A1 | 8/2007 | Zang et al. |
| 2008/0065212 | A1 | 3/2008 | Zucherman |
| 2008/0154316 | A1 | 6/2008 | Reiley |
| 2008/0195099 | A1 | 8/2008 | Minas |
| 2008/0312742 | A1 | 12/2008 | Abernathie |
| 2009/0062916 | A1 | 3/2009 | Fox |
| 2009/0177203 | A1 | 7/2009 | Reiley |
| 2009/0187247 | A1* | 7/2009 | Metcalf, Jr. .............. A61F 2/447 623/17.16 |
| 2009/0259261 | A1 | 10/2009 | Reiley |
| 2009/0318977 | A1* | 12/2009 | Di Giacomo ........ A61B 17/809 606/86 R |
| 2010/0292738 | A1 | 11/2010 | Reiley |
| 2010/0305704 | A1 | 12/2010 | Messerli et al. |
| 2011/0087296 | A1 | 4/2011 | Reiley et al. |
| 2011/0118796 | A1 | 5/2011 | Reiley et al. |
| 2011/0160866 | A1* | 6/2011 | Laurence ................ A61F 2/442 623/17.16 |
| 2011/0172780 | A1 | 7/2011 | Scheland |
| 2011/0224796 | A1* | 9/2011 | Weiland .................. B22F 10/20 623/17.16 |
| 2012/0296428 | A1* | 11/2012 | Donner ............... A61F 2/30988 623/17.11 |
| 2013/0138154 | A1 | 5/2013 | Reiley |
| 2013/0345814 | A1 | 12/2013 | Walkenhorst et al. |
| 2014/0066995 | A1 | 3/2014 | Mccormick |
| 2014/0107786 | A1 | 4/2014 | Geisler et al. |
| 2014/0114415 | A1 | 4/2014 | Tyber |
| 2016/0113770 | A1 | 4/2016 | Early et al. |

FOREIGN PATENT DOCUMENTS

| | | |
|---|---|---|
| CN | 107106218 A | 8/2017 |
| JP | 2006075598 A | 3/2006 |
| JP | 2007521885 A | 8/2007 |
| JP | 2012518499 A | 8/2012 |
| JP | 2017536160 A | 12/2017 |
| WO | WO-2010096942 A1 | 9/2010 |
| WO | WO-2016065124 A1 | 4/2016 |

OTHER PUBLICATIONS

"U.S. Appl. No. 14/520,441, Advisory Action dated Aug. 25, 2017", 3 pgs.

"U.S. Appl. No. 14/520,441, Advisory Action dated Sep. 10, 2018", 2 pgs.

"U.S. Appl. No. 14/520,441, Corrected Notice of Allowability dated May 21, 2019", 2 pgs.

"U.S. Appl. No. 14/520,441, Final Office Action dated Jun. 6, 2017", 14 pgs.

"U.S. Appl. No. 14/520,441, Final Office Action dated Jun. 29, 2018", 10 pgs.

"U.S. Appl. No. 14/520,441, Non Final Office Action dated Sep. 9, 2016", 10 pgs.

"U.S. Appl. No. 14/520,441, Non Final Office Action dated Nov. 29, 2018", 10 pgs.

"U.S. Appl. No. 14/520,441, Non Final Office Action dated Dec. 8, 2017", 12 pgs.

"U.S. Appl. No. 14/520,441, Notice of Allowance dated Apr. 3, 2019", 11 pgs.

"U.S. Appl. No. 14/520,441, Response filed Feb. 28, 2019 to Non Final Office action dated Nov. 29, 2018", 12 pgs.

"U.S. Appl. No. 14/520,441, Response filed Mar. 8, 2018 to Non Final Office Action dated Dec. 8, 2017", 12 pgs.

"U.S. Appl. No. 14/520,441, Response filed Aug. 7, 2017 to Final Office Action dated Jun. 7, 2017", 12 pgs.

"U.S. Appl. No. 14/520,441, Response filed Aug. 17, 2016 to Restriction Requirement dated Jun. 17, 2016", 9 pgs.

"U.S. Appl. No. 14/520,441, Response filed Aug. 29, 2018 to Final Office Action dated Jun. 29, 2018", 13 pgs.

"U.S. Appl. No. 14/520,441, Restriction Requirement dated Jun. 17, 2016", 9 pgs.

"Australian Application Serial No. 2015335862, First Examination Report dated May 17, 2019", 3 pgs.

"Chinese Application Serial No. 201580062728.X, Office Action dated Jan. 28, 2019", w/English translation, 19 pgs.

"Chinese Application Serial No. 201580062728.X, Response filed May 14, 2019 to Office Action dated Jan. 28, 2019", (W/ English Claims), 10 pgs.

"European Application Serial No. 15790400.4, Response filed Dec. 21, 2017 to Action dated Jun. 12, 2017", 13 pgs.

"zinternational Application Serial No. PCT/US2015/056871, International Preliminary Report on Patentability dated May 4, 2017", 7 pgs.

"International Application Serial No. PCT/US2015/056871, International Search Report dated Jan. 20, 2016", 4 pgs.

"International Application Serial No. PCT/US2015/056871, Written Opinion dated Jan. 20, 2016", 5 pgs.

"Canadian Application Serial No. 2,965,511, Office Action dated Nov. 5, 2020", 3 pgs.

"Canadian Application Serial No. 2,965,511, Response filed Jan. 6, 2021 to Office Action dated Nov. 5, 2020", 7 pgs.

"Chinese Application Serial No. 201580062728.X, Decision of Rejection dated Mar. 16, 2020", (W/ English Translation), 16 pgs.

"Chinese Application Serial No. 201580062728.X, Notice of Reexamination dated Jul. 6, 2021", (W/ English Translation), 12 pgs.

"Chinese Application Serial No. 201580062728.X, Office Action dated Aug. 9, 2019", (W/English Translation), 20 pgs.

"Chinese Application Serial No. 201580062728.X, Response filed May 20, 2020 to Decision of Rejection dated Mar. 16, 2020", (W/ English Translation of Claims), 11 pgs.

"Chinese Application Serial No. 201580062728.X, Response filed Jul. 23, 2021 to Notice of Reexamination dated Jul. 6, 2021", (W/ English Translation of Claims), 8 pgs.

"European Application Serial No. 15790400.4, Communication Pursuant to Article 94(3) EPC dated Mar. 5, 2020", 4 pgs.

"European Application Serial No. 15790400.4, Response filed Jun. 30, 2020 to Communication Pursuant to Article 94(3) EPC dated Mar. 5, 2020", 24 pgs.

"Japanese Application Serial No. 2017-522185, Final Notification of Reasons for Refusal dated Apr. 21, 2020", (W/ English Translation), 6 pgs.

"Japanese Application Serial No. 2017-522185, Notification of Reasons for Refusal dated Aug. 20, 2019", (W/ English Translation), 17 pgs.

"Japanese Application Serial No. 2017-522185, Response filed Jul. 13, 2020 to Final Notification of Reasons for Refusal dated Apr. 21, 2020", (W/ English Translation of Claims), 13 pgs.

(56) References Cited

OTHER PUBLICATIONS

"Japanese Application Serial No. 2017-522185, Response filed Nov. 17, 2019 to Notification of Reasons for Refusal dated Aug. 20, 2019", (W/ English Translation of Claims), 18 pgs.

* cited by examiner

METHOD AND APPARATUS FOR BONE FIXATION

CLAIM OF PRIORITY

This application is a divisional of U.S. patent application Ser. No. 14/520,441, filed on Oct. 22, 2014, which issued as U.S. Pat. No. 10,383,733 on Aug. 20, 2019, the benefit of priority of which is claimed hereby, and which is incorporated by reference herein in its entirety.

FIELD

The present disclosure relates generally to orthopedic surgical devices and techniques and, more particularly, to fixation devices and techniques for correction, repair, reconstruction and/or fixation/fusion of bone segments.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Surgical or medical procedures are often performed on a body, for example, a human body or anatomy, to repair, reconstruct and/or replace various portions thereof. For example, after trauma, there may be a need to fix bone segments together to immobilize the segments and permit healing. There may also be a need for fusion of bone segments or reconstruction of a bone or bone segments in connection with an osteotomy. Conventional implants that can be utilized in connection with such procedures do not provide optimal surfaces for bone in-growth and/or require separate, additional fixation systems, which require additional surgical instruments and procedures. Accordingly, there remains a need for improvement in the relevant art.

SUMMARY

This section provides a general summary of the disclosure, and is not a comprehensive disclosure of its full scope or all of its features.

In one aspect, an orthopedic implant for use with fixation of a joint or fracture is provided in accordance with various aspects of the present disclosure. In an exemplary implementation, the orthopedic implant can include a tapered member and at least one fixation member. The tapered member can be adapted for placement in association with one or more bone segments. The tapered member can have a longitudinally extending body that defines an upper surface portion, an opposed lower surface portion and opposed first and second sides. In one exemplary implementation, at least the opposed first and second sides can be formed of porous metal and can have a porous outer surface. The at least one fixation member can be integrally formed with the tapered member and can extend laterally outwardly from the tapered member body. The at least one fixation member can be adapted to secure the implant to the one or more bone segments to provide fixation of the one or more bone segments relative to the tapered member.

In another aspect, an orthopedic implant for use with fixation of a joint or fracture is provided in accordance with various aspects of the present disclosure. In an exemplary implementation, the orthopedic implant can include a tapered member and first and second fixation members. The tapered member can be adapted for placement in association with one or more bone segments. The tapered member can have a longitudinally extending body defining an upper surface portion, an opposed lower surface portion and opposed first and second sides. In one exemplary implementation, at least the first and second sides can be formed of porous metal and having a porous outer surface. The first fixation member and the second fixation member can be integrally formed with the tapered member and can extend laterally outwardly from the respective first and second sides of the tapered member body. The first and second fixation members can be adapted to provide fixation of the one or more bone segments relative to the tapered member in a first direction parallel to a longitudinal axis of the tapered member body and in a second direction perpendicular to the longitudinal axis.

In yet another aspect, a method for fixation or fusion of bone segments is provided in accordance with various aspects of the present disclosure. In an exemplary implementation, the method can include forming a cavity in a first bone segment and a second bone segment about a joint or fracture between the first and second bone segments. An implant having a porous metal construct can be inserted into the cavity. The implant can include a tapered member and first and second fixation members. The tapered member can have a longitudinally extending body that defines an upper surface portion, an opposed lower surface portion and opposed first and second sides. The first and second fixation members can extend relative to the first and second sides. In an exemplary implementation, at least the first and second sides can be formed of porous metal and can have a porous metal outer surface. The implant can be positioned in the cavity such that a first longitudinal axis of the tapered member body is substantially aligned with a second longitudinal axis of the joint or fracture. With the insertion of the implant, the first and second bone segments can be fixed in a first direction parallel to the longitudinal axis and in a second direction transverse to the first direction.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

Figure 11:
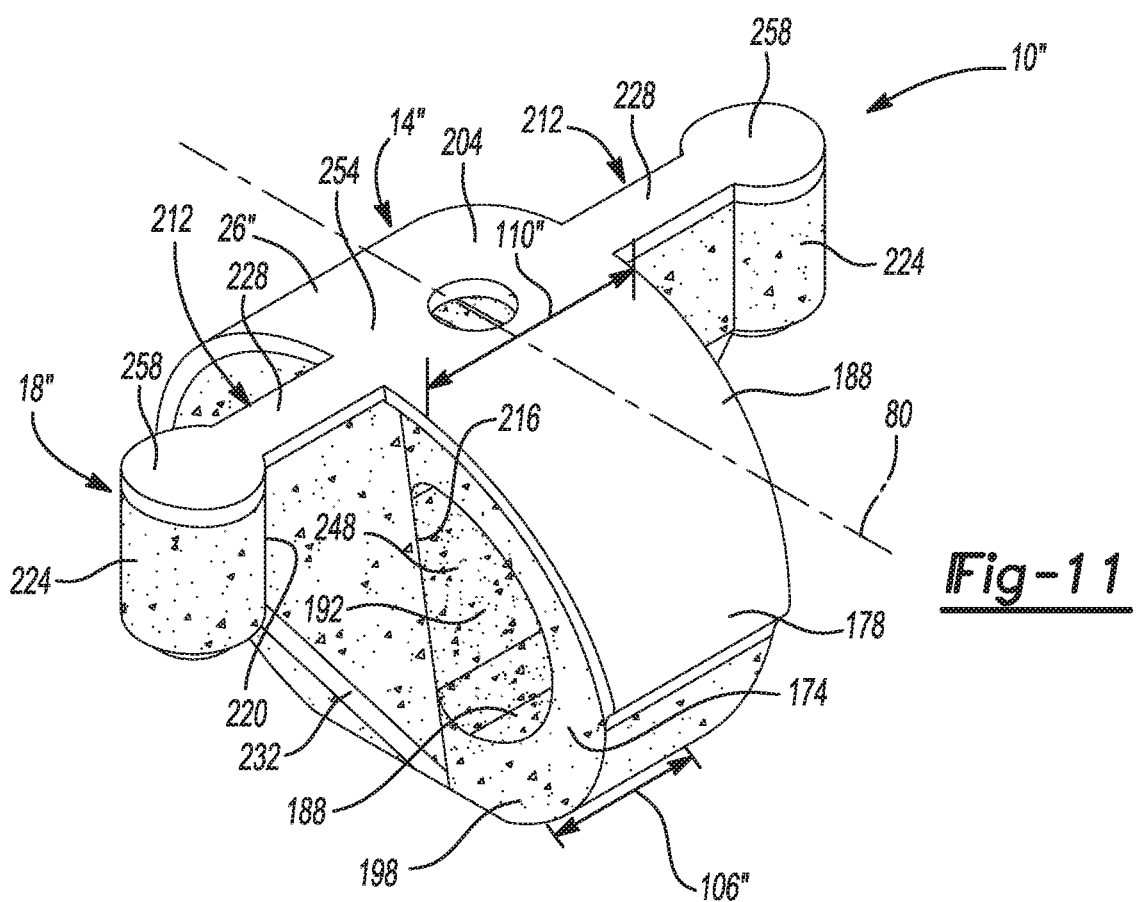
FIG. 11 is a top perspective view of an exemplary bone fixation device in accordance with various aspects of the present disclosure.
Figure 13:
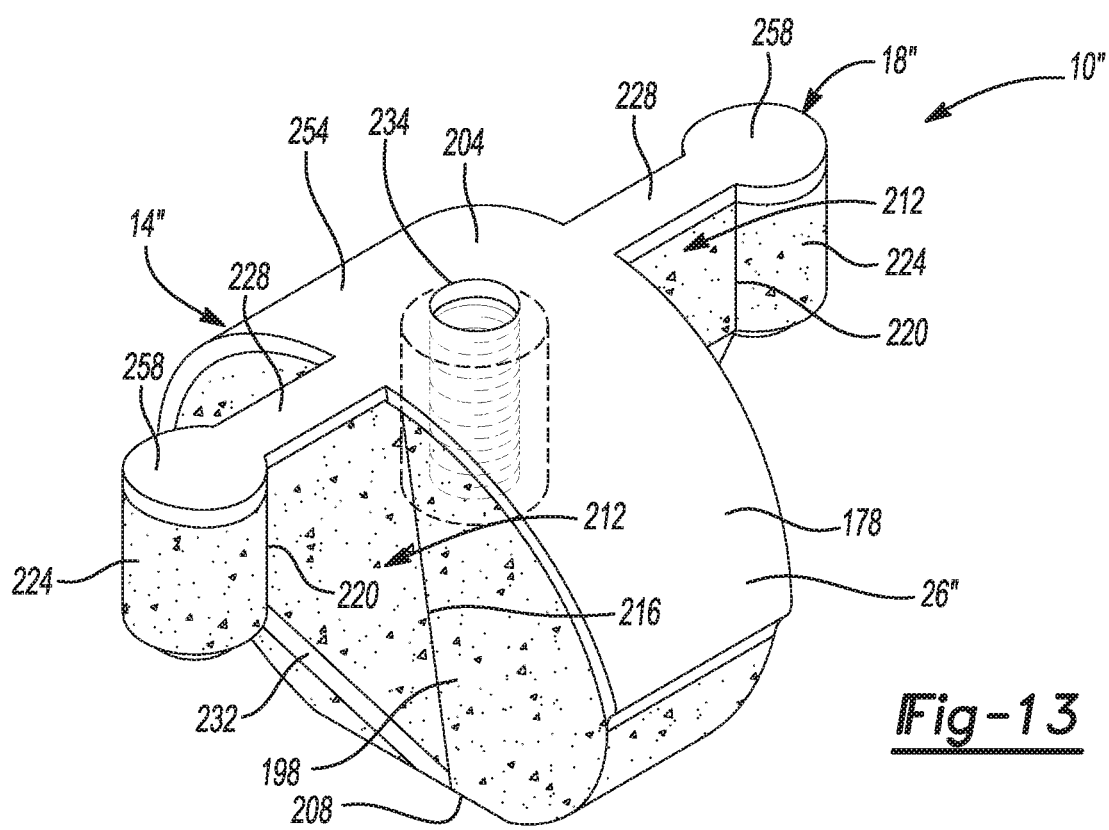
FIG. 13 is a top perspective view of an exemplary bone fixation device in accordance with various aspects of the present disclosure.
Figure 14:
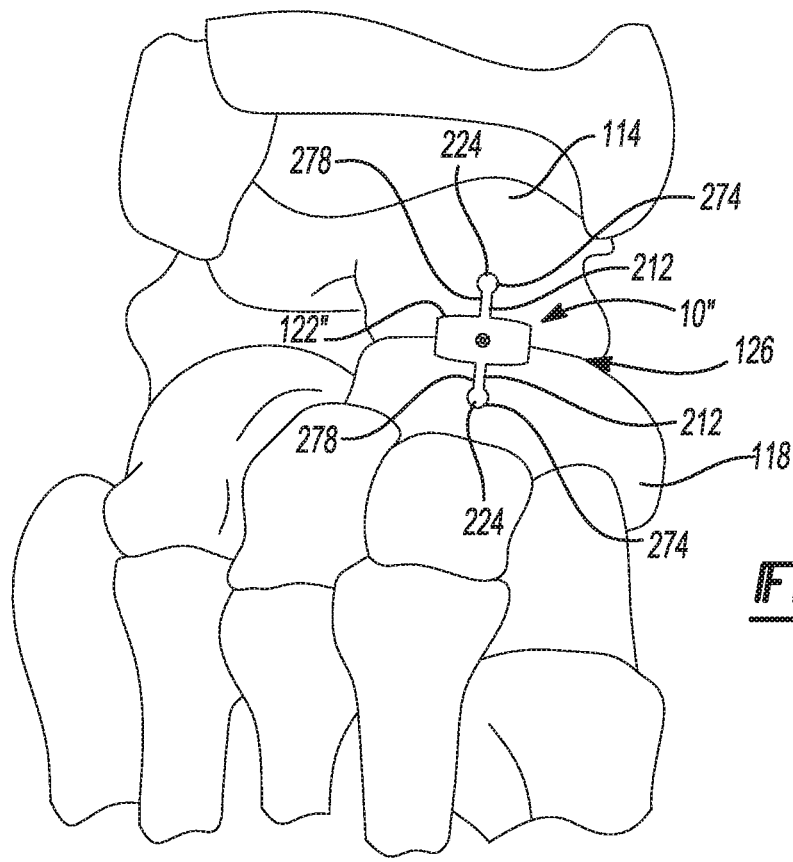
Figure 15:
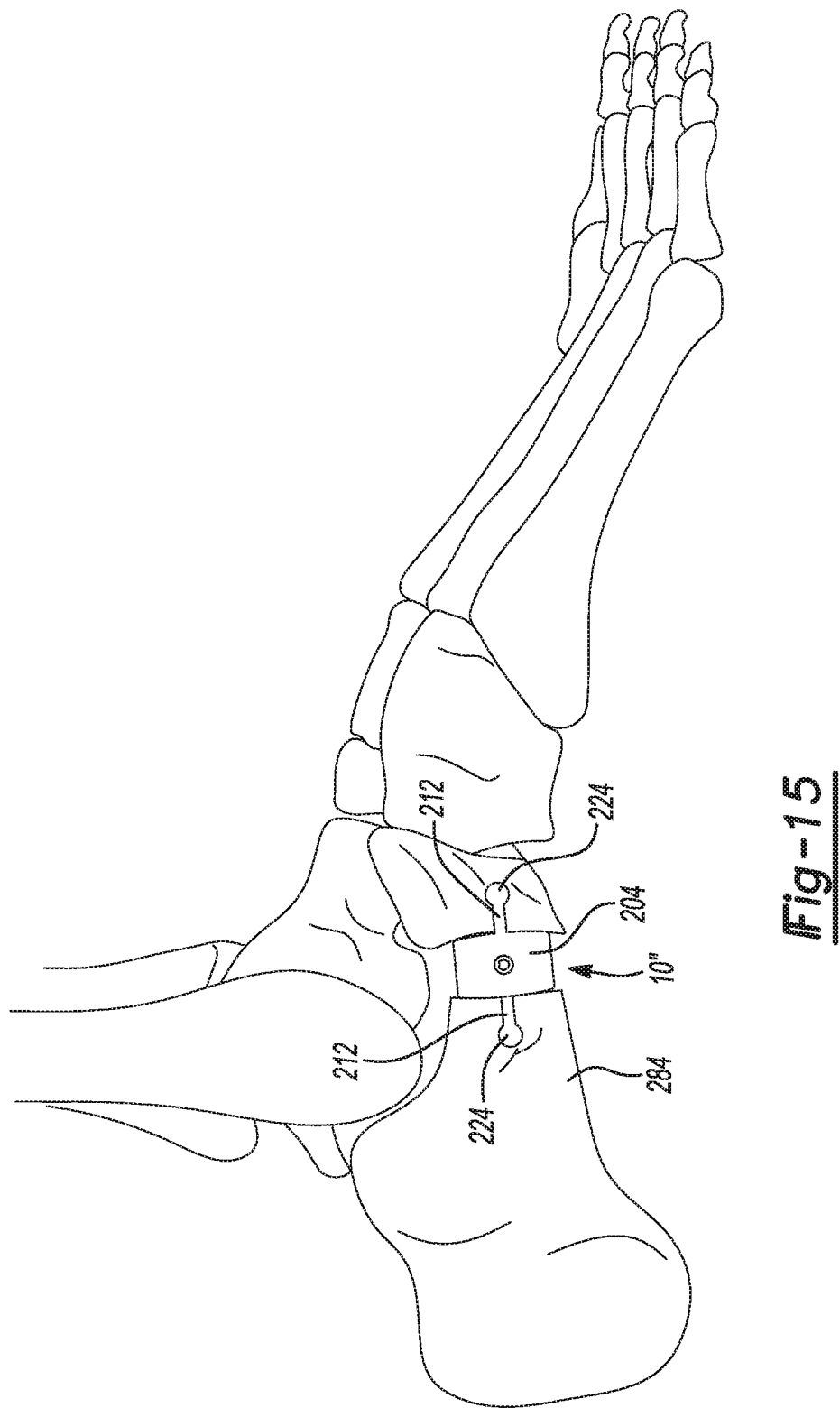

FIG. 14 is a view of an exemplary surgical technique illustrating the bone fixation device of FIG. 11 or 13 implanted relative to a Talo-Navicular joint in accordance with various aspects of the present disclosure; and FIG. 15 is a view of an exemplary surgical technique illustrating the bone fixation device of FIG. 11 or 13 utilized in an Evans osteotomy procedure in accordance with various aspects of the present disclosure.

DETAILED DESCRIPTION

The following description is merely exemplary in nature and is not intended to limit the present disclosure, its application, or uses. Although the following description is related generally to methods and apparatus for bone fixation in a foot, it will be appreciated that the methods and apparatus discussed herein can be applicable to various bones and/or joints of the anatomy and can be utilized in various fixation procedures or techniques.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The present teachings provide bone fixation devices and methods for using the same to facilitate bone fixation and healing. In an exemplary aspect, the bone fixation devices can be utilized for fracture fixation, fixation of two adjacent bone segments (e.g., joint fusion), and/or for stabilization/reconstruction of a bone or bone segments, including in connection with an osteotomy or the like. In this regard, for the sake of brevity, the devices discussed herein will be referred to as fixation devices and it will be understood that such fixation devices can perform a stabilization function as well as a fixation function between two bone segments, a fusion function between two or more bones or bone segments and/or reconstruction of a bone or bone segments. As used herein, "bone segments" can refer to two segments of the same bone (e.g., relative to a fracture line and/or osteotomy) or adjacent bones (e.g., of a joint). Further, while the discussion will continue with reference to fixation of the Talo-Navicular joint, it will again be appreciated that the fixation devices discussed herein can be utilized for fixation, fusion and/or reconstruction/repair of various different small bones and/or joints, such as in the hand or foot.

With initial reference to FIGS. 1 and 2-4, an exemplary bone fixation device according to various aspects of the present teachings is shown and generally identified at reference numeral 10. As will be discussed in greater detail below, the bone fixation device 10 can, in one exemplary implementation, provide for stabilization of bone segments, such as the Talus and Navicular bones of the Talo-Navicular joint, as well as fixation of the bones with a single, unitary structure. In one exemplary aspect, the bone fixation device 10 can include a stabilization or tapered member and an integral fixation arrangement. As will also be discussed in greater detail below, the bone fixation device 10 can include a porous metal portion or region and can also be provided in the form of a kit having various different sizes and/or configurations of the bone fixation device 10 with or without associated instrumentation. In one exemplary aspect, the bone fixation device 10 can be a manufactured as a custom and/or patient-specific implant.

Figure 1:
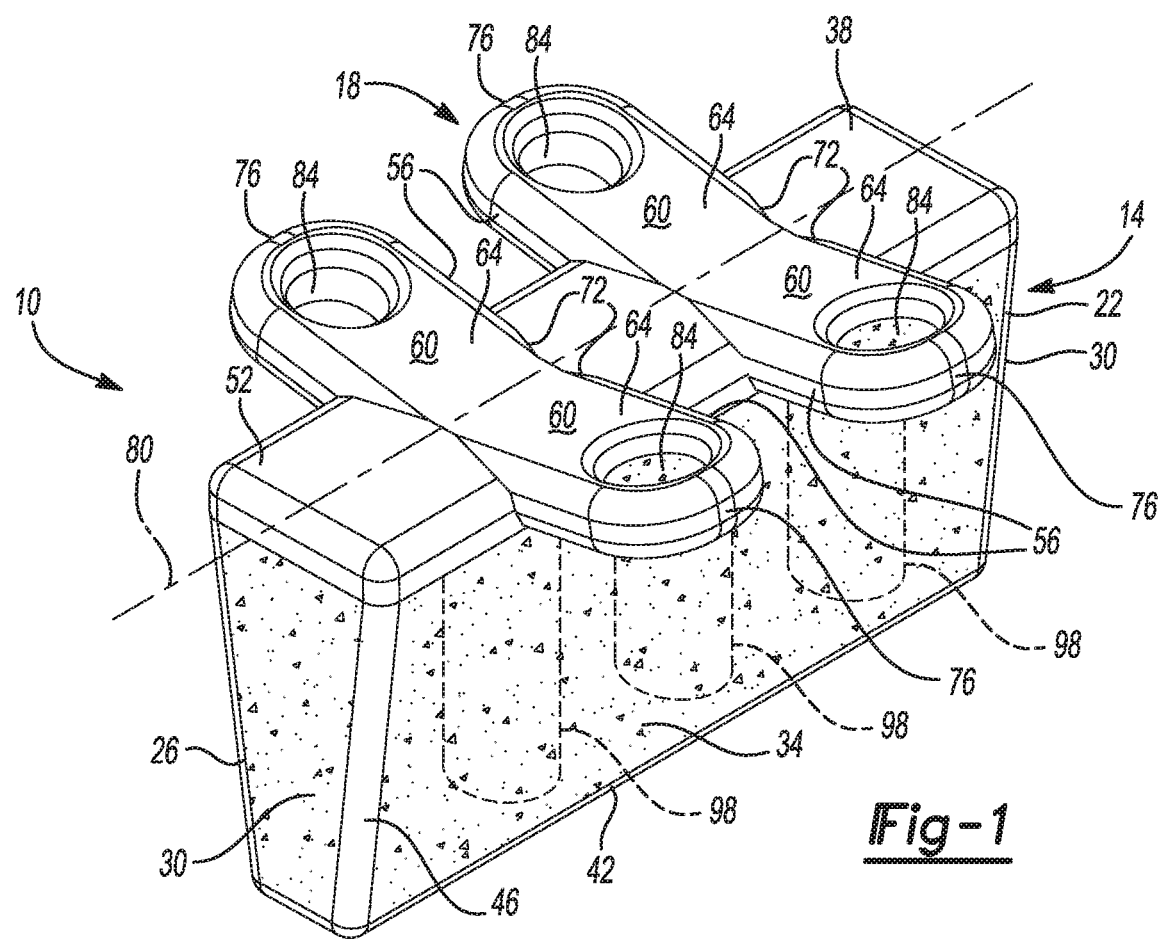
FIG. 1 is a top perspective view of an exemplary bone fixation device in accordance with various aspects of the present disclosure.

In one exemplary implementation, the bone fixation device 10 includes a tapered or wedge member or portion 14 and a fixation arrangement 18 constructed as a unitary device, as can be seen for example in FIG. 1. The wedge member 14 can be provided in the form of a wedge shaped structure 22 integrally formed with the fixation arrangement 18. As briefly mentioned above, the bone fixation device 10 can be provided in the form of a kit that includes various different sizes and/or configurations of the wedge member 14 and/or fixation arrangement 18.

The wedge structure 22 can include a longitudinally extending body 26 extending between and forming opposed longitudinal ends 30, as well as opposed sides 34, an upper or top surface portion 38 and an opposed lower or bottom surface portion 42. The wedge structure 22 can be formed of a biocompatible alloy, such as a titanium alloy. In one exemplary implementation, the bone fixation device 10 can be formed using an additive manufacturing process with a titanium alloy core and a porous metal titanium alloy structure and outer surface for the wedge member 14. For example, the longitudinal ends 30, opposed sides 34 and bottom surface 42 of the wedge shaped structure 22 can be formed as a porous metal construct or structure. In another exemplary implementation, the bottom surface 42 and/or corners 46 between the sides 34 and ends 30 can be formed of solid or substantially solid titanium alloy, as shown for example in FIG. 1. In this example, the leading edge or surface of the bone fixation device 10, namely the bottom surface 42, can be formed from solid metal alloy for, in one exemplary aspect, increased surface strength for insertion purposes.

In one exemplary implementation, the porous metal structure can be a formed from a titanium alloy using an additive manufacturing process, such as with OsseoTi™, which is commercially available from Biomet Manufacturing, LLC (Warsaw, Ind., USA). Briefly, however, OsseoTi is highly biocompatible, has high corrosion resistance and includes a highly interconnected porous architecture that mimics the porous structure of human cancellous bone, which can enhance bone integration and in-growth. In one exemplary implementation, OsseoTi can include a porous construct with a porosity of 70%.

In the exemplary implementation illustrated in FIGS. 1-4, the fixation arrangement 18 can include a plate member or portion 52 having one or more fixation members 56 extending therefrom. In one implementation, the plate member 52 can be a solid or substantially solid structure integrally formed with the wedge shaped stabilization member 14 to form the unitary bone fixation device 10. The plate member 52 and fixation members 56 can include a smooth or substantially smooth outer surface. In the example illustrated, the plate member 52 can form the upper structure of the bone fixation device 10, including the upper surface portion 38 of the stabilization member 14. The fixation members 56 can extend outwardly from the plate member 52 and can provide for securing the bone fixation device 10 to the associated bone segments.

In accordance with an aspect of the present disclosure, the fixation members 56 can include outwardly extending arms 60 having an upper or top surface 64, an opposed bottom surface 68 configured to face and/or engage bone, an inner end or area 72 where the arm 60 extends from the plate member 52, and an opposed outer end 76. In the example illustrated, the arms 60 can extend outwardly relative to each longitudinal side of plate member 52. For example, the arms 60 can extend perpendicular or substantially perpendicular or transverse to a longitudinal axis 80 of plate member 52 and bone fixation device 10.

Figure 3:
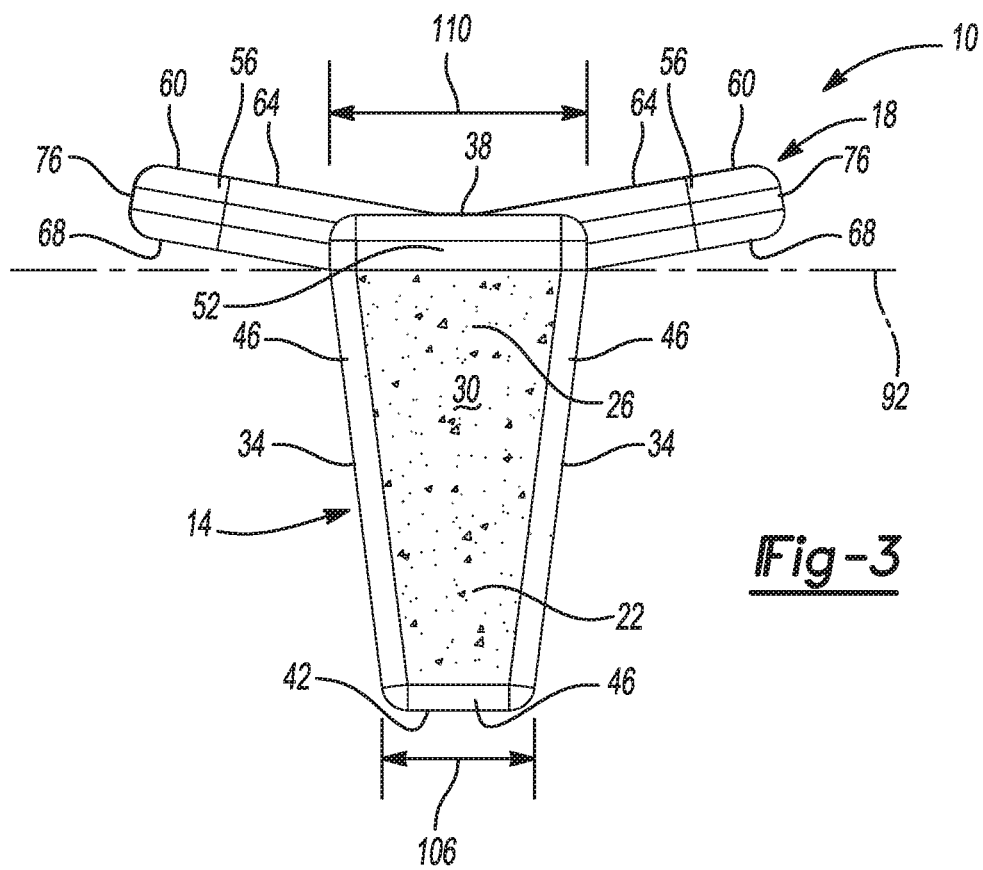
FIG. 3 is a side or end view of the exemplary bone fixation device of FIG. 1 in accordance with various aspects of the present disclosure.
Figure 4:
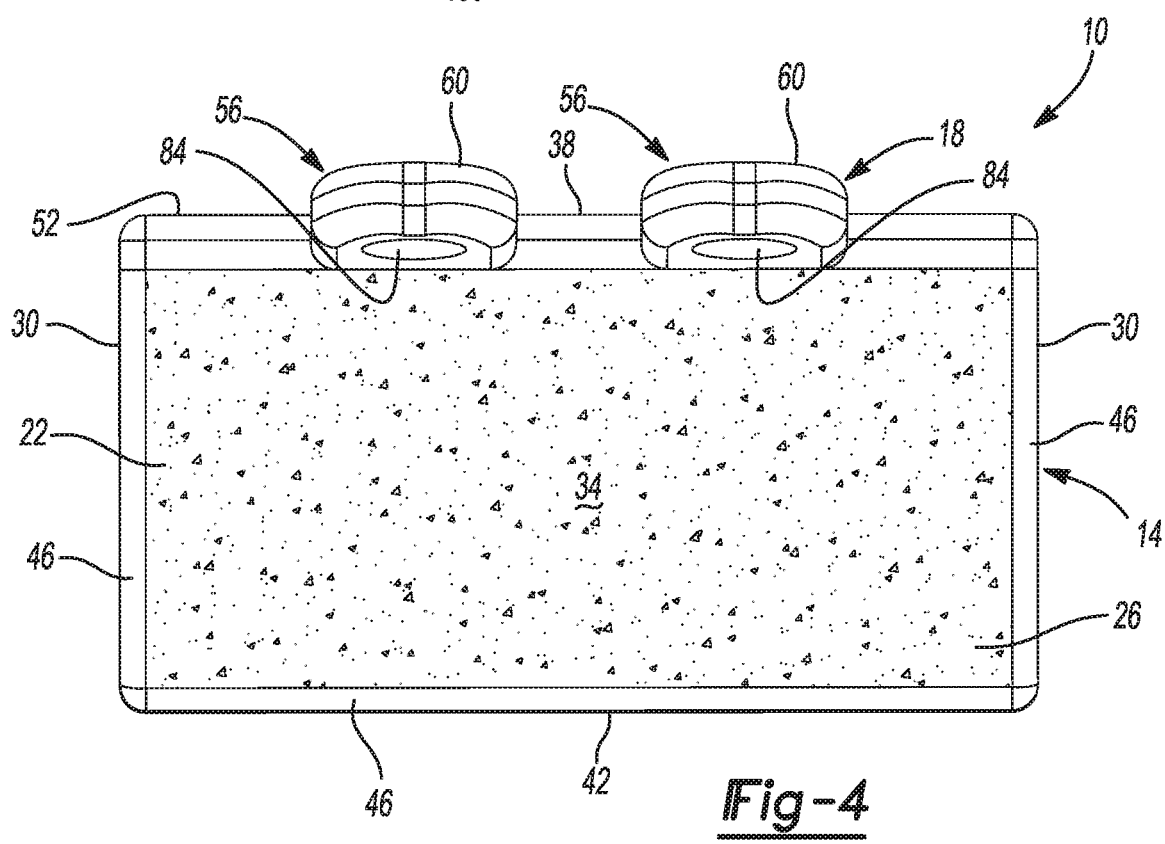
FIG. 4 is a side view of the exemplary bone fixation device of FIG. 1 in accordance with various aspects of the present disclosure.

The arms 60 can each define an aperture 84 proximate the outer end 76 and configured to receive a fastener 88 (FIG. 6) for fixing or securing the bone fixation device 10 to the bone segments. In one exemplary implementation, the arms 60 can be inclined upwardly relative to the plate member 52, as can be seen for example in FIG. 3. For example, the arms 60 can be inclined upwardly at an acute angle relative to a plane 92 extending through and parallel to plate member 52, as also shown in FIG. 3. In the example illustrated in FIGS. 1-4, the bone fixation device 10 includes four arms 60. It will be appreciated, however, that the bone fixation device 10 can include more or less arms 60 depending on, for example, the size of the bone fixation device 10 and/or its intended use.

As briefly discussed above, the wedge member or portion 14 of the bone fixation device 10 can include the wedge shaped structure 22 formed from porous metal, such as OsseoTi, through the additive manufacturing process. In one exemplary implementation, the wedge shaped structure 22 can be formed around a core, such as one or more core members 98 extending from and integrally formed with plate member 52, as shown in FIG. 1. The core members 98, in the example illustrated, are cylindrical members formed from the titanium alloy used to form the bone fixation device 10. It will be appreciated, however, that the wedge member 14 can be formed with or without the core or support members 98, which can take the form of various different shapes, including cylindrical.

The sides 34 of the wedge member 14 can be tapered or angled outwardly to form the wedge shaped structure 22. For example, a width 106 of the bottom surface 42 can be smaller than a width 110 of the top surface 38 such that the sides 34 are angled outwardly at acute angles to form the wedge shaped structure 22, as shown for example in FIG. 3.

In the example illustrated, the sides 34 can be planar. The amount of taper of the wedge shaped stabilization member 14 can be varied along with the size of the bone fixation device 10 to accommodate the type and location of the bone segments to be treated as well as individual anatomy. The different sizes and configurations of the bone fixation device 10 can be provided in kit form or as a patient-specific implant, as discussed above.

Figure 1A:
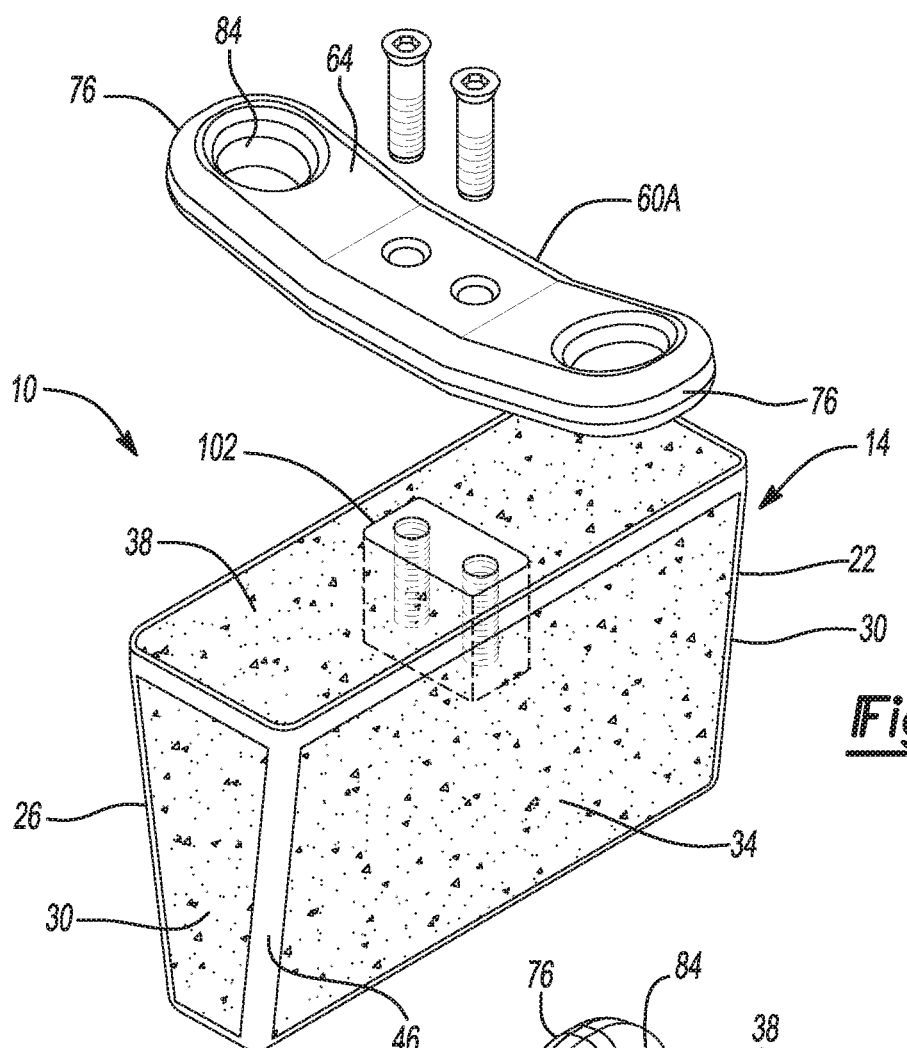
FIG. 1A is a top perspective view of an exemplary bone fixation device in accordance with various aspects of the present disclosure.
Figure 2:
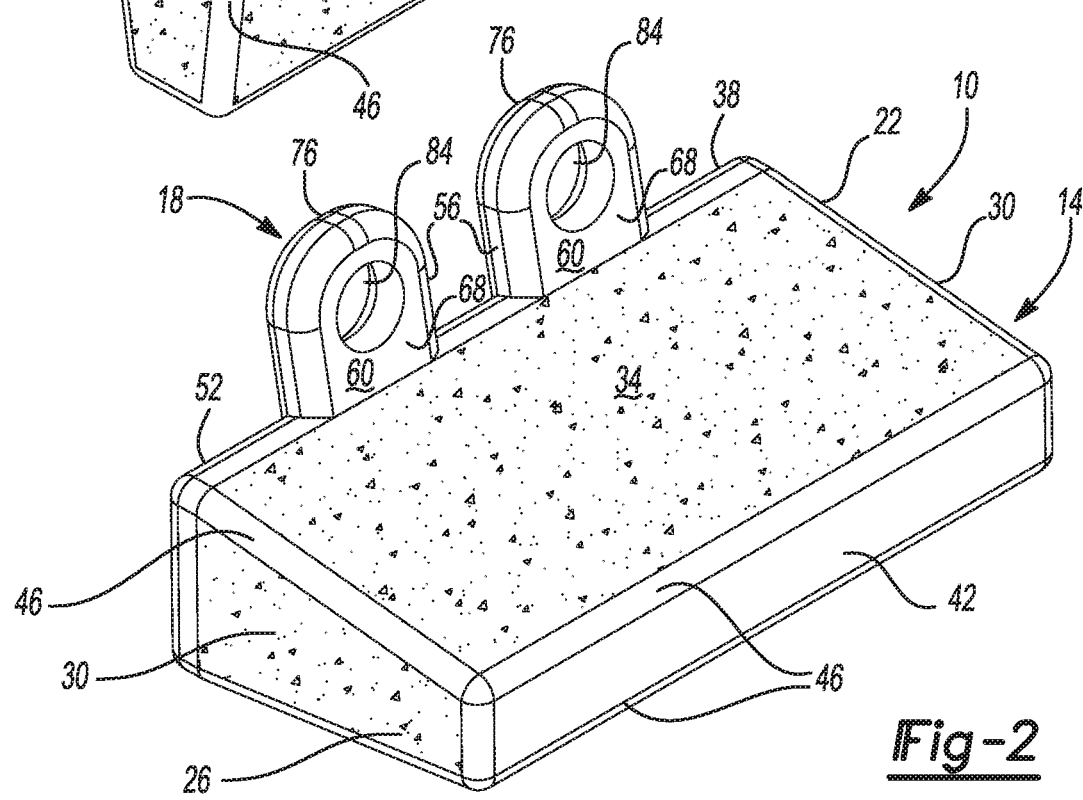
FIG. 2 is a side perspective view of the exemplary bone fixation device of FIG. 1 in accordance with various aspects of the present disclosure.

With additional reference to FIG. 1A, bone fixation device 10 can be provided with optionally removable arms 60A. Removable arms 60A can be the same or substantially the same as removable arm 60 such that only differences will be discussed below. In this exemplary implementation, a solid metal threaded insert 102 can be formed in body 26 surrounded by the porous metal construct and opening to the top surface 38, which can be formed as solid metal or porous metal construct (as shown). Each removable arm 60A can include one or more holes for receiving a fastener therethrough for removably securing the removable arm 60A to the threaded insert 102. It will be appreciated that other fixation devices discussed herein that include integral fixation members and optionally have those fixation members removably secured through use of a similar fastening arrangement.

Figure 6:
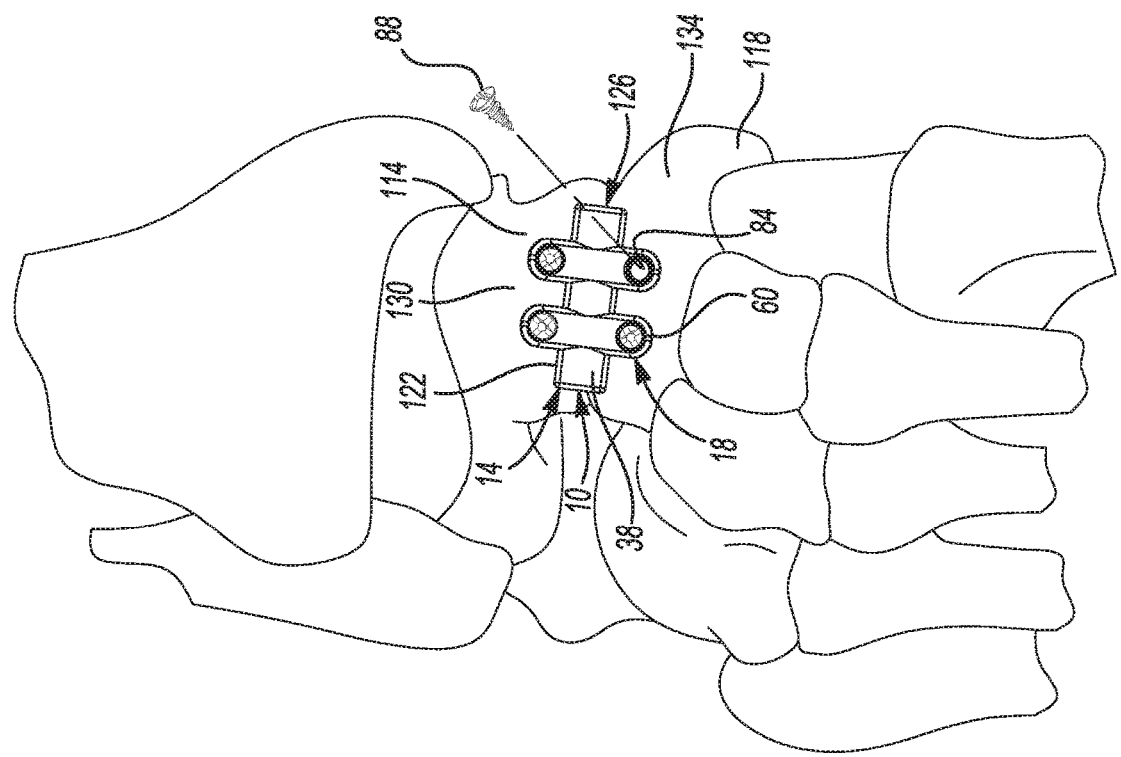
FIGS. 5-6 are views of an exemplary surgical technique illustrating the bone fixation device of FIG. 1 implanted relative to a Talo-Navicular joint in accordance with various aspects of the present disclosure.
Figure 5:
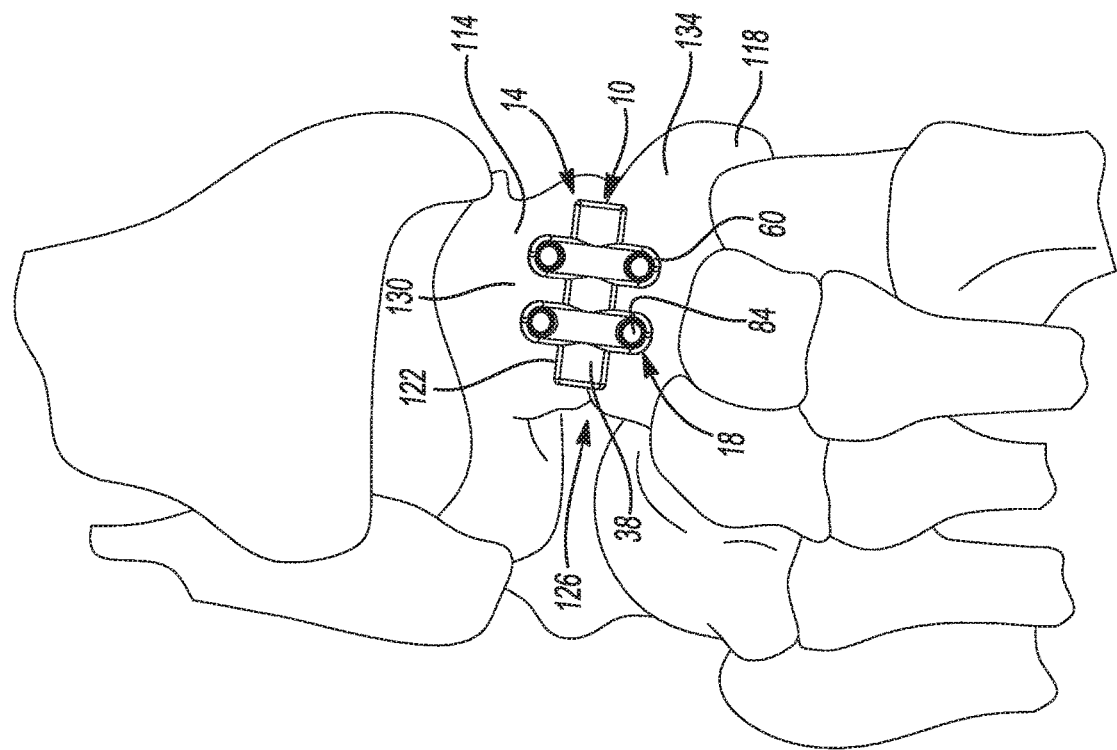

As briefly discussed above, the bone fixation device 10 can be utilized in various surgical techniques, such as for fracture fixation, fixation of two adjacent bone segments (e.g., joint fusion), and/or for stabilization/reconstruction of a bone or bone segments, including in connection with an osteotomy or the like. With additional reference to FIG. 5 and continuing reference back to FIGS. 1-4, use of the bone fixation device 10 in an exemplary fixation technique of two bone segments will now be discussed in greater detail. In this example, the bone fixation device 10 is used for fixation of the Talus 114 and Navicular 118 bones that form the Talo-Navicular joint 126, as shown in FIGS. 5 and 6.

The bone segments (i.e., the Talus 114 and Navicular bones 118) can be prepped for implantation of the bone fixation device 10. A high speed burr or other suitable bone cutting or removal device can remove a portion of bone from the Talus bone 114 and the Navicular bone 118 to create a pocket or cavity 122 for receipt of the bone fixation device 10 in or relative to the Talo-Navicular joint 126, as shown in FIG. 5. The cavity 122 can be formed with a longitudinal axis parallel or substantially parallel to the joint 126, such as parallel to a longitudinal axis of the joint 126. With the bones 114, 118 prepared, the bone fixation device 10 can be inserted into the cavity 122 such that the longitudinal axis of the bone fixation device 10 is parallel to or substantially parallel to the joint 126. In one exemplary aspect, the bone fixation device 10 can be positioned in the cavity 122 such that the upper surface 38 is flush or below outer surfaces 130, 134 of the respective Talus and Navicular bones 114, 118. In a technique where the upper surface portion 38 is positioned below the outer bone surfaces 130, 134, the angled nature of the arms 60 can provide for such positioning while also allowing for fixation to the Talus and Navicular bones 114, 118.

With the bone fixation device 10 inserted and the Talo-Navicular joint 126 in the desired orientation for fixation (i.e., joint fusion), the fasteners 88 can be inserted through apertures 84 of arms 60 and into the Talus and Navicular bones 114, 118 to provide for stabilization and fixation/fusion of the joint 126 with a single device. In this exemplary technique, the arms 60 can be positioned perpendicular or substantially perpendicular to the joint 126. Through use of this single bone fixation device 10, the surgical technique of the present disclosure reduces surgical steps, reduces the number of implants required and thus the complexity of the operating room preparation and associated procedure, as well as reduces the time required to perform the procedure. In addition, the porous metal structure of the wedge member 14 can provide for enhanced bone in-growth and accelerated healing.

Figure 7:
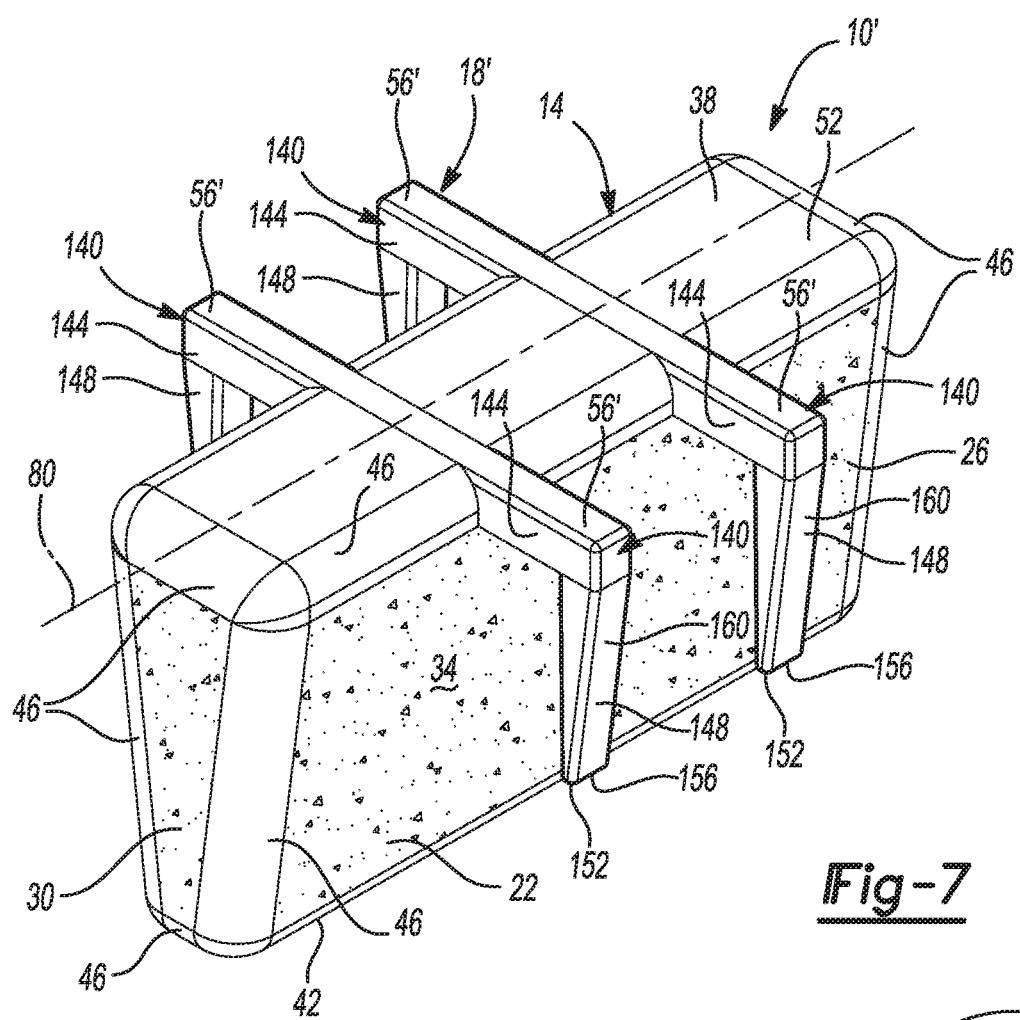
FIG. 7 is a top perspective view of an exemplary bone fixation device in accordance with various aspects of the present disclosure.
Figure 8:
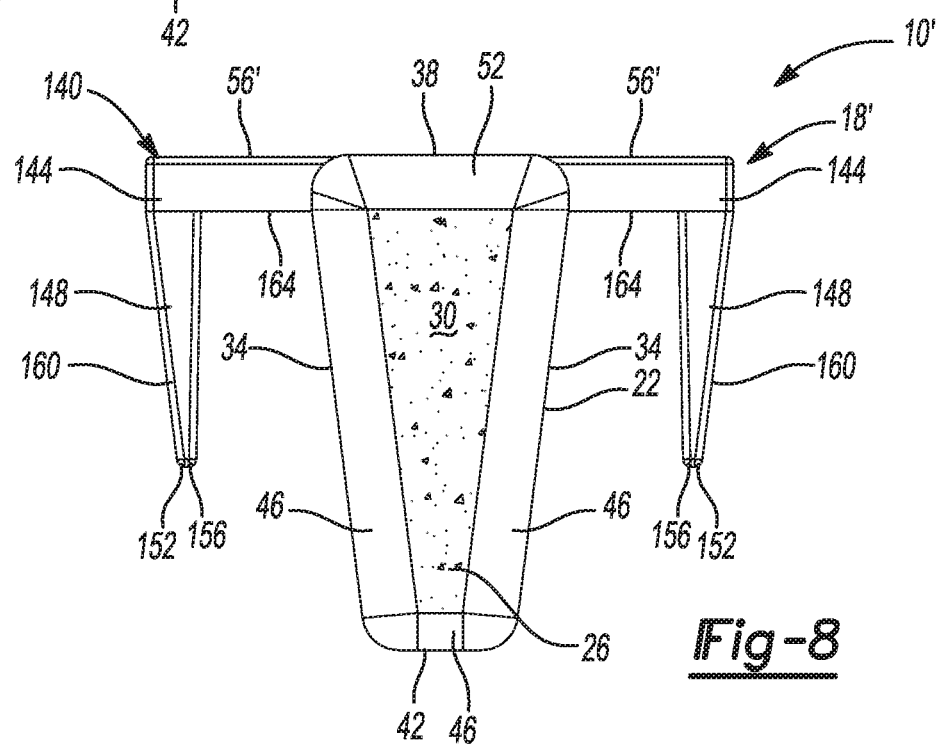
FIG. 8 is a side or end view of the exemplary bone fixation device of FIG. 7 in accordance with various aspects of the present disclosure.
Figure 9:
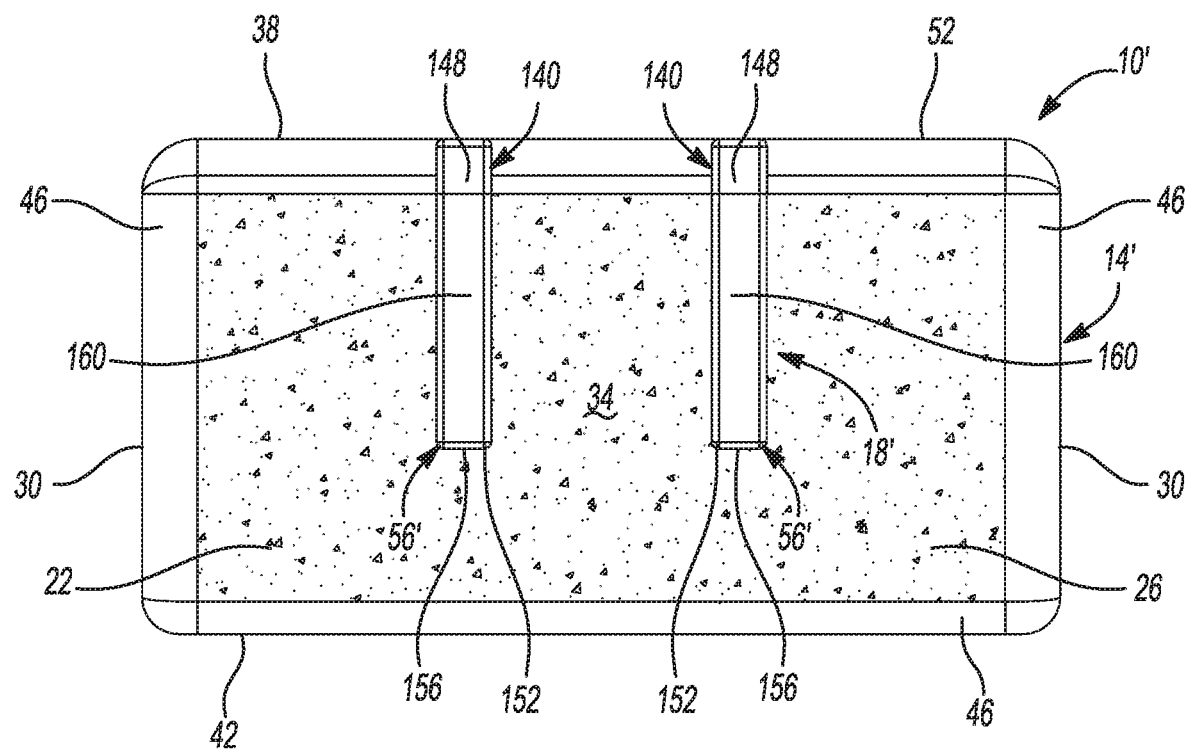
FIG. 9 is a side view of the exemplary bone fixation device of FIG. 1 in accordance with various aspects of the present disclosure.

Turning now to FIGS. 7-9 and with continuing reference to FIGS. 1-6, another example of a bone fixation device 10' will now be discussed. Bone fixation device 10' can be similar to bone fixation device 10 such that only differences will be discussed in detail and like reference numerals can refer to like or similar components and/or features. The bone fixation device 10' can include a fixation arrangement 18' in the form of one or more fixation members 56' extending from and integrally formed with plate member 52, as shown for example in FIG. 7.

In one exemplary aspect, the fixation members 56' can be in the form of staples 140 having an upper portion 144 and a lower portion 148. The upper portion 144 can extend from each longitudinally opposed side of plate member 52 and can integrally transition into the lower portion 148. In the example illustrated, the upper portion 144 can be parallel to or substantially parallel to the upper surface portion 38 of bone fixation device 10. In one aspect of this example, the upper portion 144 can be flush or substantially flush with upper surface portion 38, as shown for example in FIG. 8. The lower portion 148 can be perpendicular or substantially perpendicular to the upper portion 144 and can have an end 152 that terminates in a distal point or tip 156 configured to pierce or penetrate bone. In one exemplary aspect, the lower portion 148 can include a tapered structure 160 that terminates in the point 156. The lower portion 148 can be spaced apart from the longitudinally extending body 26 by the upper portion 144.

With additional reference to FIG. 10, use of the bone fixation device 10' in an example fixation procedure of two bone segments will now be discussed. Similar to bone fixation device 10 discussed above, bone fixation device 10' can be utilized in various surgical techniques, such as for fracture fixation of bone segments, fixation of two adjacent bone segments (e.g., joint fusion), and/or for stabilization/reconstruction of a bone or bone segments, such as in connection with an osteotomy or the like. In the example shown in FIG. 10, the bone fixation device 10' is again used for fixation (i.e., joint fusion) of the Talus and Navicular bones 114, 118 that form the Talo-Navicular joint 126.

The bone segments (i.e., the Talus and Navicular bones 114, 118) can be prepped for implantation of the bone fixation device 10 in a similar manner as for bone fixation device 10. With the cavity 122 prepared and the Talo-Navicular joint 126 in the desired orientation for fixation, the bone fixation device 10' can be inserted into the cavity 122 until the point 156 of the staples 140 contacts the associated Talus and Navicular bones 114, 118. Similar to bone fixation device 10 discussed above, bone fixation device 10' can be inserted into cavity 122 such that the longitudinal axis is parallel to or substantially parallel to joint 126.

Figure 10:
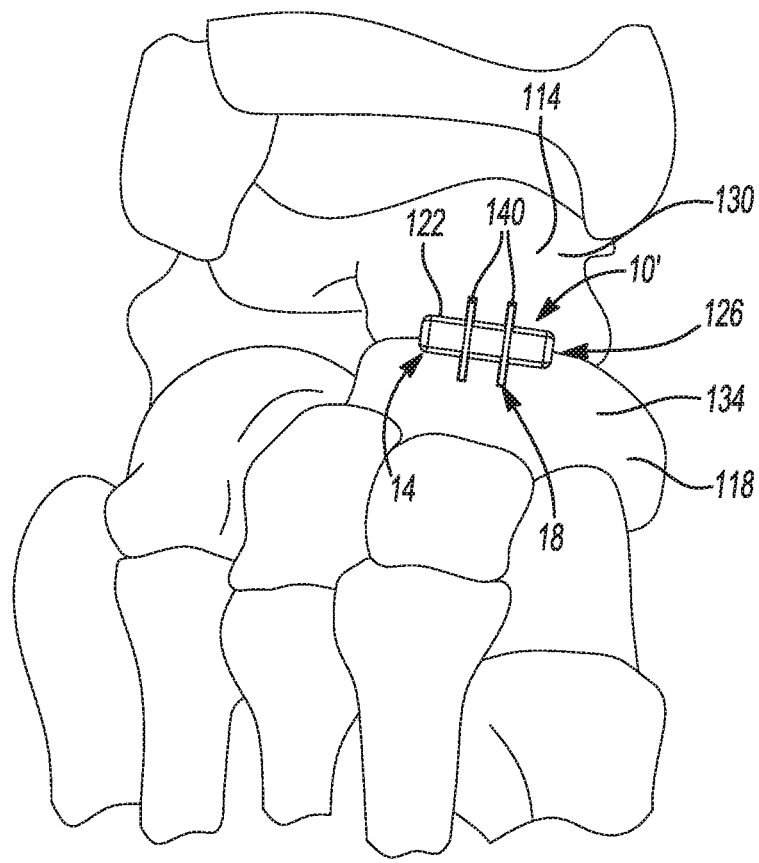
FIG. 10 is a view of an exemplary surgical technique illustrating the bone fixation device of FIG. 7 implanted relative to a Talo-Navicular joint in accordance with various aspects of the present disclosure.

An impact device can be used to apply a force to the top surface portion 38 to drive the staples 140 into the Talus and Navicular bones 114, 118, as shown in FIG. 10 for stabilization and fixation of joint 126. It will be appreciated that such an impact device can also be used in connection with implanting the various other fixation devices discussed herein. The staples 140 can be positioned perpendicular or substantially perpendicular to the joint 126. In one exemplary aspect, the bone fixation device 10' can be inserted and/or driven until a lower surface 164 (FIG. 8) of the upper portion 144 engages or substantially engages the outer surfaces 130, 134 of the Talus and Navicular bones 114, 118. This bone fixation device 10' can provide for stabilization and fixation/fusion of the joint 126 with a single device and a single insertion step. In addition, the porous metal structure of the stabilization portion or member 14 can provide for enhanced bone in-growth and accelerated healing similar to or the same as bone fixation device 10.

In one exemplary aspect, the staples 140 can be round or substantially round such that the lower portion 148 includes a conical or substantially conical tapered structure 160. In this exemplary aspect, bores can be formed in the bone for the staples 140, such as with a guide that assists with forming the cavity 122 and the holes for the lower portion 148 of the staples 140. For example, the guide can provide an alignment template as well as provide for the proper size and placement of the cavity 122 and preformed holes for the round staples 140.

Figure 12:
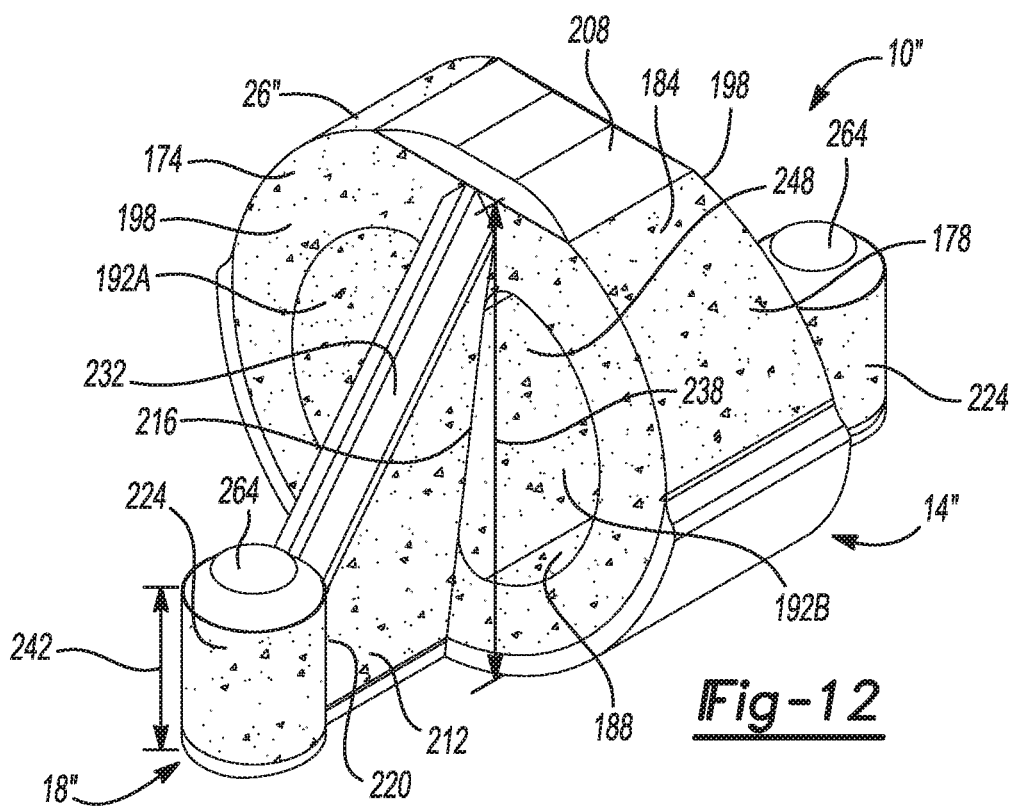
FIG. 12 is a bottom perspective view of the exemplary bone fixation device of FIG. 1 in accordance with various aspects of the present disclosure.

Turning now to FIGS. 11-13, another example of a bone fixation device 10" is shown and will now be discussed. Various aspects of bone fixation device 10" can be similar to bone fixation devices 10 and 10' such that only differences will be discussed in detail and like reference numerals can refer to like or similar components and/or features. Bone fixation device 10" can also be a unitary device formed from a titanium alloy similar to bone fixation devices 10 and 10'. Bone fixation device 10" can include a tapered or wedge member 14" and a fixation arrangement 18", as shown for example in FIG. 11. In the exemplary implementation illustrated, the wedge member 14" can extend along a longitudinal axis 80 of the bone fixation device 10" and the fixation arrangement 18" can extend perpendicular to or substantially perpendicular to the longitudinal axis 80.

The wedge member 14" can include a longitudinally extending body 26" that defines a ring or ring-like structure 174 having a circular or oval shape 178 that extends along longitudinal axis 80, as shown for example in FIGS. 11 and 12. The ring 174 can include or define an outer wall or surface 184 and an inner wall or surface 188 that defines a hollow interior or pocket 192 for additional bone-ingrowth. The ring 174 can also include or define opposed side surfaces or edges 198, an upper surface 204 and an opposed lower or leading surface 208, as also shown in FIGS. 11 and 12.

Similar to the wedge members 14, 14' discussed above, the wedge member 14" can include angled or tapered sides 198 such that the wedge member body 26" includes a tapered or wedge shape in cross section taken perpendicular to the longitudinal axis 80. For example, a width 106" of the lower surface or side 208 can be smaller than a width 110" of the upper surface or side 204 such that the sides 198 are angled outwardly at acute angles to form the wedge shaped structure, as shown for example in FIGS. 11 and 12. The amount of taper of the wedge shaped member 14" can be varied along with the size of the bone fixation device 10" to accommodate the type and location of the bone segments to be treated as well as individual anatomy. The different sizes and configurations of the bone fixation device 10" can be provided in kit form, as discussed above.

The fixation arrangement 18" can include bridge members 212 laterally extending from each side 198 of the wedge member body 26". In one exemplary implementation, each bridge member 212 can include a first end 216 integrally formed with and extending from the sides 198 of ring 174 and a body or span extending to an opposed second end 220 coupled to or terminating into an integrally formed dowel member 224. The bridge members 212 can also include an upper side or surface 228 extending from the upper surface or side 204 and a lower side or surface 232 extending from the lower surface or side 208. In one exemplary implementation, the upper surface 228 can be flush with or substantially flush with the upper surface 204.

In the exemplary implementation illustrated, the lower surface 232 can be angled upwardly toward the upper surface 228 such that each bridge member 212 forms a triangular or substantially triangular shape along an axis extending perpendicular to or substantially perpendicular to the longitudinal axis 80. In other words and with particular reference to FIG. 12, the first end 216 can have a first length 238 substantially equal to a length of the wedge member 14" from the upper surface 204 to the lower surface 208, and the second end 220 can have a second length 242 less than the first length 238. In one exemplary implementation, the body 26" can include a central member or portion 248 between and connecting the bridge members 212, as can be seen in FIGS. 11 and 12. In this example, the central portion 248 can essentially bisect the interior pocket 192 into two portions 192A, 192B on longitudinally opposite sides of central portion 248.

The dowel members 224 can include a cylindrical shape and can have a length substantially equal to a length of the second end 220, as shown for example in FIGS. 11 and 12. In this exemplary implementation, the dowel members 224 and the second end 220 of bridge members 212 can be spaced apart from a plane extending parallel to the bottom surface 208 of wedge member 14".

Similar to the bone fixation devices 10 and 10' discussed above, bone fixation device 10" can also be formed from an additive manufacturing process to include both solid or substantially solid titanium alloy portions and porous metal portions, such as OsseoTi. For example and with reference to FIGS. 11-12, bone fixation device 10" can include a solid or substantially solid top portion or plate member 254 having a smooth or substantially smooth outer surface. The top portion 254 can form the upper surface 204 of the wedge member 14" and the upper surfaces 228 of the bridge members 212 as well as an upper surface 258 of the dowel members 224, as shown for example in FIG. 11. In the example illustrated, the top portion 254 can extend from upper surface 204 partially around the ring 174, as also shown in FIG. 11. With particular reference to FIG. 12, the lower surface 208 of the wedge member 14" as well as the bottom surfaces 232 of the bridge members and a bottom surface 264 of the dowel members 224 can also be formed from a solid or substantially sold form of the titanium alloy and can include a smooth or substantially smooth outer surface. The remaining portions of the ring 174, bridge members 212 and dowel members 224, as well as the central portion 248, can be formed as a porous metal construct.

With particular reference to FIG. 13 and continuing reference to FIGS. 11-12, an alternative example of the bone fixation device 10" is shown where the body 26" similarly includes the oval or circular shape 178, but alternatively does not include the hollow interior region 192. In this example implementation, the body 26" can be formed as a porous metal construct with or without a core member, as can be seen in FIG. 13. FIG. 13 also illustrates an optional threaded hole 234 formed as part of a solid metal structure extending from the upper surface or side 204 and surrounded by the porous metal construct. The threaded hole 234 can be used, in one exemplary implementation, to facilitate threadably removably coupling an insertion/removal instrument to bone fixation device 10". The other structure and/or features of this example of bone fixation device 10" can be the same or substantially the same as the example discussed with reference to FIGS. 11-12.

With additional reference to FIG. 14 and continuing reference to FIGS. 11-13, use of the bone fixation device 10" in an example fixation procedure of two bone segments will now be discussed. Similar to bone fixation devices 10 and 10' discussed above, bone fixation device 10" can also be utilized in various surgical fixation techniques, such as for fracture fixation of bone segments, fusion of two adjacent bone segments (e.g., joint fusion), and/or for stabilization/reconstruction of a bone or bone segments, including in connection with an osteotomy or the like. In the example shown in FIG. 14, the bone fixation device 10" is again shown in use for fixation (i.e., joint fusion) of the Talo-Navicular joint 126.

As with the techniques discussed above, the Talus and Navicular bones 114, 118 can be prepared adjacent the joint 126 for receipt of the wedge member 14". For the joint fixation technique illustrated, a drill guide or similar device corresponding to the size of the bone fixation device 10" selected for the procedure can be positioned on or relative to the Talus and Navicular bones 114, 118 to indicate the size and position of the cavity 122" and holes 274 for the dowel members 224. For a fracture fixation technique, the bone segments can be compressed and maintained in a compressed state before forming the cavity 122" and holes 274. The template can also include a pattern for forming cuts 278 in the Talus and Navicular bones 114, 118 for receipt of the bridge members 212. In an alternative implementation, the bridge members 212 can be formed with a minimal thickness in the direction of the longitudinal axis 80 and with a pointed lower surface 232 configured to cut into bone. In this example implementation, the cuts for the bridge members can be formed so as to provide an interference fit or may not be utilized.

Returning to the example technique depicted and discussed with reference to FIG. 14, the bone fixation device 10" can be inserted into the prepared bones such that the wedge member 14", bridge members 212 and dowel members 224 are positioned in the cavity 122", holes 274 and cuts 278, respectively. In this exemplary technique, the bridge members 212 are positioned perpendicular or substantially perpendicular to the joint 126. The implanted bone fixation device 10" can substantially prevent or eliminate distraction of the bone segments (e.g., Talus and Navicular bones 114, 118) forming the joint 126 through use of the dowel members 224, as well as substantially prevent or eliminate side-side motion or micro-motion of the bones forming joint 126 through use of the bridge members 212. More particularly, the dowel members 224 can prevent anterior-posterior distraction of the Talus and Navicular bones 114, 118 and the bridge members 212 can prevent medial-lateral shifting of the Talus and Navicular bones 114, 118.

The bone fixation device 10" thus can provide for stabilization and fixation/fusion of the Talo-Navicular joint 126 (or two bone segments) with a single device. Through use of this single device, the associated surgical technique can reduce the surgical steps required (e.g., one insertion step for stabilization/reconstruction and fixation), reduce the number of implants required and thus the complexity of the operating room preparation and associated procedure, as well as reduce the time required to perform the procedure. In addition, the porous metal structure of the stabilization portion or wedge member 14 can provide for enhanced bone in-growth and accelerated healing.

With additional reference to FIG. 15, the bone fixation device 10" is shown in connection with an Evan's open wedge osteotomy procedure. As can be seen in FIG. 15, the bone fixation device 10" can be implanted at the osteotomy site of the calcaneal bone 284 proximal to or at the calcaneal-cuboid joint. Bone fixation device 10" can be implanted into the prepared bone site in a similar manner as discussed above with reference to FIG. 14.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. An orthopedic implant, comprising:
a tapered member adapted for placement in association with one or more bone segments, the tapered member having a longitudinally extending body defining an upper planar surface portion, an opposed lower surface portion and opposed first and second sides, at least the opposed first and second sides being formed of porous metal and having a porous metal outer surface; and
at least one fixation member integrally formed with the tapered member and extending laterally outwardly from the tapered member body, the at least one fixation member adapted to secure the implant to the one or more bone segments to provide fixation of the one or more bone segments relative to the tapered member, wherein the at least one fixation member includes a staple member extending from the upper planar surface portion, wherein the staple member includes a first leg member extending laterally outwardly from the upper planar surface portion and defining a first leg member upper planar surface and a first leg member lower surface which is parallel to the first leg member upper planar surface, and a second leg member extending downward from the first leg member, the second leg member having a tapered structure and including an inner surface facing the tapered member, the inner surface being substantially perpendicular to the first leg member and perpendicular to the upper planar surface portion and extending in a direction from the upper planar surface portion towards the lower surface portion, and an outer surface facing away from the tapered member, the outer surface extending obliquely towards the inner surface in a direction from the upper planar surface portion towards the lower surface portion and meeting with the inner surface to form a distal tip, wherein the outer surface extends in an oblique direction all the way from the first leg member lower surface to the distal tip, the second leg member including a first side surface extending between the inner surface and the outer surface and a second side surface extending between the inner surface and the outer surface opposite the first side surface, wherein the first side surface and the second side surface are parallel to each other from a top of the second leg member to a bottom of the second leg member.

2. The implant of claim 1, wherein the opposed first and second sides of the tapered member body taper outwardly from the lower surface portion to the upper planar surface portion such that the tapered member includes a wedge-shaped structure with the tapered member body at the lower surface portion having a smaller width than the tapered member body at the upper planar surface portion.

3. The implant of claim 1, wherein the tapered member body further includes longitudinally opposed ends formed of porous metal and having a porous outer surface, and wherein the upper planar surface portion and the lower surface portion are formed as solid structure portions of the tapered member body having a substantially smooth outer surface.

4. The implant of claim 3, wherein the at least one fixation member includes a plurality of fixation members, at least one of the plurality of fixation members extending laterally outwardly relative to the first side in a first direction and at least another one of the plurality of fixation members extending laterally outwardly relative to the second side in a second opposite direction.

5. The implant of claim 4, wherein the at least one and the at least another one of the plurality of fixation members are formed as a solid structure extending from the upper planar surface portion.

6. The implant of claim 1, wherein the staple member includes a first staple portion extending laterally outwardly relative to the first side in a first direction and a second staple portion extending laterally outwardly relative to the second side in a second opposite direction.

7. The implant of claim 6, wherein the first and second staple portions each include a first leg member extending laterally outwardly from and substantially flush with the upper planar surface portion, and a second leg member substantially perpendicular to the first leg member and extending in a direction from the upper planar surface portion to the lower surface portion.

8. The implant of claim 7, wherein each second leg member is spaced apart from the tapered member body and is sized and shaped to comprise a length less than a length of the tapered member body from the upper planar surface portion to the lower surface portion.

* * * * *